US012329550B2

(12) United States Patent
Spottiswoode et al.

(10) Patent No.: US 12,329,550 B2
(45) Date of Patent: Jun. 17, 2025

(54) SYSTEMS AND METHODS FOR LOW FIELD MR/PET IMAGING

(71) Applicant: Siemens Medical Solutions USA, Inc., Malvern, PA (US)

(72) Inventors: Bruce Spottiswoode, Knoxville, TN (US); Sven Zuehlsdorff, Oak Brook, IL (US); Matthias J. Schmand, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 394 days.

(21) Appl. No.: 17/904,786

(22) PCT Filed: May 6, 2020

(86) PCT No.: PCT/US2020/070028
§ 371 (c)(1),
(2) Date: Aug. 23, 2022

(87) PCT Pub. No.: WO2021/225640
PCT Pub. Date: Nov. 11, 2021

(65) Prior Publication Data
US 2023/0049556 A1    Feb. 16, 2023

(51) Int. Cl.
*A61B 6/03* (2006.01)
*G01R 33/48* (2006.01)
*G06T 5/50* (2006.01)

(52) U.S. Cl.
CPC ............ *A61B 6/037* (2013.01); *G01R 33/481* (2013.01); *G06T 5/50* (2013.01); *G06T 2207/10088* (2013.01)

(58) Field of Classification Search
None
See application file for complete search history.

(56) References Cited

U.S. PATENT DOCUMENTS

| 10,102,451 | B2* | 10/2018 | Han | G06F 18/214 |
| 2006/0052685 | A1* | 3/2006 | Cho | G01R 33/20 600/407 |
| 2011/0007959 | A1* | 1/2011 | Schulz | G06T 7/38 382/131 |

(Continued)

FOREIGN PATENT DOCUMENTS

JP    2015516194    6/2015

OTHER PUBLICATIONS

Huang, Y., Song, T., Xu, J., Chen, Y., & Zhuang, X. (2019). KLDivNet: an unsupervised neural network for multi-modality image registration. arXiv preprint arXiv:1908.08767 (Year: 2019).*

(Continued)

*Primary Examiner* — Anand P Bhatnagar

(57) ABSTRACT

Systems and methods of PET attenuation correction using low-field MR image data includes receiving a first set of image data and a set of low-field magnetic resonance (MR) image data. An attenuation correction map is generated from the low-field MR image data using a first trained neural network. At least one attenuation correction process is applied to the first set of image data based on the attenuation correction map to generate at least one clinical attenuation-corrected image.

20 Claims, 10 Drawing Sheets

(56) References Cited

U.S. PATENT DOCUMENTS

| | | | | |
|---|---|---|---|---|
| 2011/0123083 A1* | 5/2011 | Ojha | ............... | G01R 33/46 |
| | | | | 382/131 |
| 2011/0235884 A1* | 9/2011 | Schreibmann | ......... | A61B 6/037 |
| | | | | 382/131 |
| 2016/0128592 A1* | 5/2016 | Rosen | ................. | A61B 5/389 |
| | | | | 600/411 |
| 2016/0320466 A1* | 11/2016 | Berker | ............ | G01R 33/56509 |
| 2020/0126231 A1* | 4/2020 | Hu | ..................... | G06T 11/005 |

OTHER PUBLICATIONS

J. O. Blumhagen, R. Ladebeck, M. Fenchel, and K. Scheffler, "Mr-based field-of-view extension in mr/pet: b0 homogenization using gradient enhancement (huge)," Magnetic Resonance in Medicine, vol. 70, No. 4, pp. 1047-1057, Nov. 2012. doi:10.1002/mrm. 24555 (Year: 2012).*

B. Yang and J. Tang, "Learning-Based Attenuation Correction for Brain PET/MRI Using Artificial Neural Networks, " 2017 IEEE Nuclear Science Symposium and Medical Imaging Conference (NSS/MIC), Atlanta, GA, USA, 2017, pp. 1-4, doi: 10.1109/NSSMIC. 2017.8532971 (Year: 2017).*

Blanc-Durand, P., Khalife, M., Sgard, B., Kaushik, S., Soret, M., Tiss, A., El Fakhri, G., Habert, M. O., Wiesinger, F., & Kas, A. (2019). Attenuation correction using 3D deep convolutional neural network for brain 18F-FDG PET/MR: Comparison with Atlas, ZTE and CT based attenuation correction. (Year: 2019).*

M. Hofmann et al., "MRI-based attenuation correction for PET/MRI: A novel approach combining pattern recognition and Atlas registration," Journal of Nuclear Medicine, vol. 49, No. 11, pp. 1875-1883, Oct. 2008 (Year: 2008).*

Wang, W. F., Ngo, F. Q., Chen, J. C., Huang, R. M., Chou, K. L., & Liu, R. S. (2003). PET-MRI image registration and fusion using artificial neural networks. Biomedical Engineering: Applications, Basis and Communications, 15(03), 95-99 (Year: 2003).*

Cao Xiaohuan et al: Deep Learning Based Inter-modality Image Registration Supervised by Intra-modality Similarity11 , Sep. 15, 2018 (Sep. 15, 2018), 12th European Conference on Computer Vision, ECCV 2012; [Lecture Notes in Computer Science], pp. 55-63.

International Search Report for Corresponding PCT Application No. PCT/US2020/070028, received Dec. 3, 2020.

* cited by examiner

SYSTEMS AND METHODS FOR LOW FIELD MR/PET IMAGING

TECHNICAL FIELD

This application relates generally to nuclear imaging and, more particularly, to hybrid magnetic resonance (MR) and positron emission tomography (PET) imaging scanners.

BACKGROUND

Multi-modality imaging systems perform diagnostic scans using multiple modalities, such as, for example, magnetic resonance (MR/MRI), computed tomography (CT), positron emission tomography (PET), and/or single photon emission computed tomography (SPECT). Multiple modalities are combined to provide complimentary and/or overlapping clinical information. For example, MR scanning generally provides soft tissue morphological data and provides greater resolution of structural and functional characteristics of soft tissue, etc. PET scanning generally has a lower resolution but provides more useful information regarding the functional condition of the body tissues and systems such as the cardiovascular system. PET scanning is superior for indicating the presence of tumors or decreased blood flow to certain organs or areas of the body. The complementary strengths of two or more imaging modalities can be provided simultaneously by performing both methods in a single apparatus and imaging session.

Current hybrid (e.g., multi-modality) imaging systems, such as PET/MR or PET/CT systems are prohibitively expensive. For example, PET/MR imaging systems are typically only accessible (i.e., financially viable) for research sites. Thus, improvements that can reduce the cost of the hardware system as well as the installation and/or operational costs are desired.

SUMMARY

In some embodiments, a computer-implemented method is disclosed. The computer-implemented method includes the steps of receiving a first set of image data and a set of low-field magnetic resonance (MR) image data; generating an attenuation correction map from the low-field MR image data using a first trained neural network; applying at least one attenuation correction process to the first set of image data based on the attenuation correction map to generate at least one clinical attenuation-corrected image.

In some embodiments, a system is disclosed. The system includes a first imaging modality, a low-field MR imaging modality, and a computer. The computer is configured to receive a first set of image data from the first imaging modality and a set of low-field magnetic resonance (MR) image data from the low-field MR imaging modality; generate an attenuation correction map from the low-field MR image data using a first trained neural network; apply at least one attenuation correction process to the first set of image data based on the attenuation correction map to generate at least one clinical attenuation-corrected image.

In some embodiments, a non-transitory computer readable medium is disclosed. The non-transitory computer readable medium stores instructions configured to cause a computer system to execute the steps of: receiving a first set of image data and a set of low-field magnetic resonance (MR) image data; generating an attenuation correction map from the low-field MR image data using a first trained neural network; apply at least one attenuation correction process to the first set of image data based on the attenuation correction map to generate at least one clinical attenuation-corrected image.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts. The drawing figures are schematic and they are not intended to show actual dimensions or proportions.

DETAILED DESCRIPTION

Figure 1:
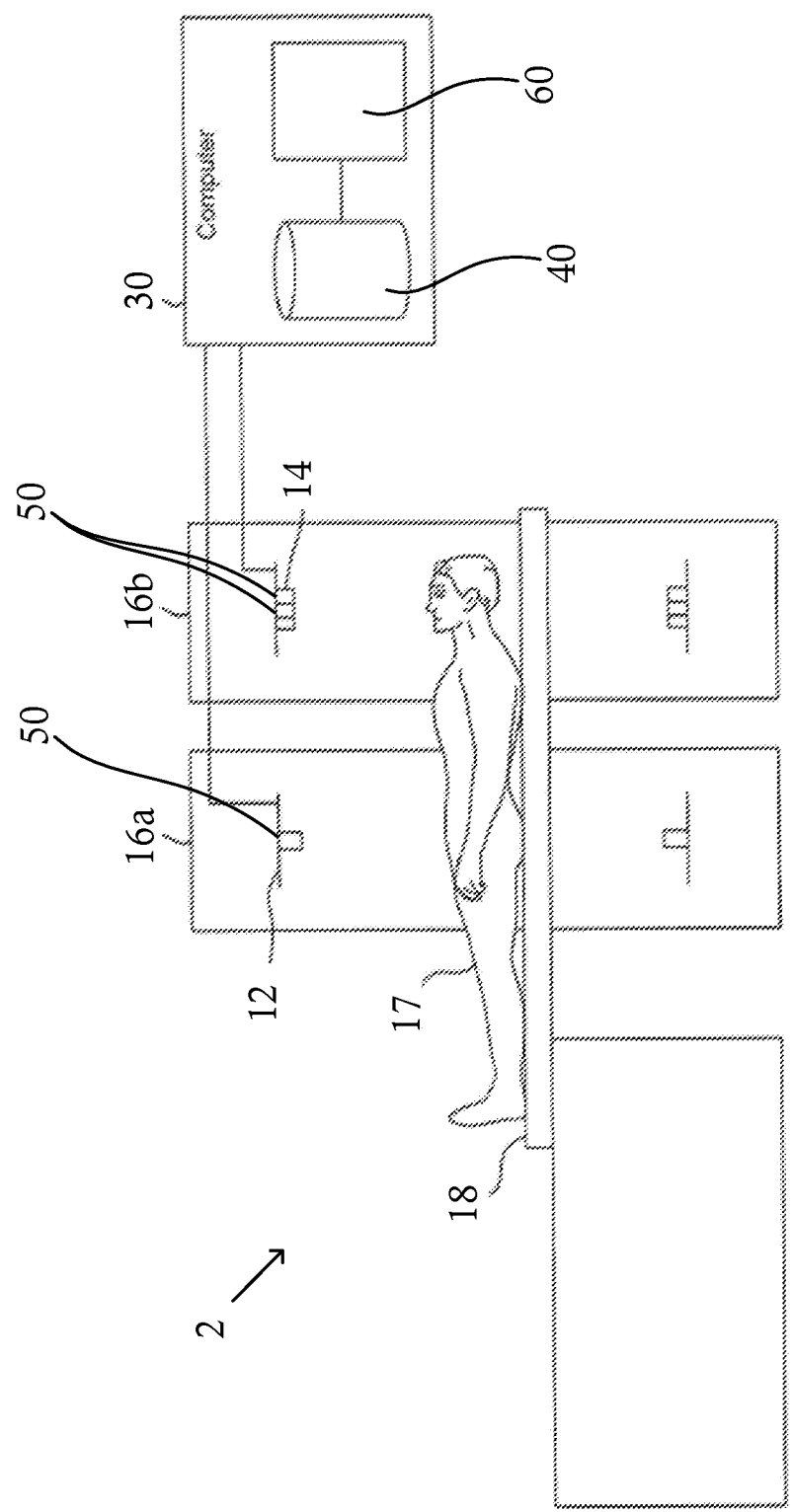
FIG. 1 illustrates a nuclear imaging system, in accordance with some embodiments.

This description of the exemplary embodiments is intended to be read in connection with the accompanying drawings, which are to be considered part of the entire written description. In the description, relative terms should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are operatively connected or attached to one another either directly or indirectly through intervening structures, including physical, electrical, optical, or other attachments or relationships, unless expressly described otherwise.

In various embodiments, systems and methods for attenuation correction of image data, such as PET image data, using low-field MR image data is disclosed. At least one trained neural network is configured to receive the low-field MR image data and spatially register the low-field MR image data with the PET image data. The registered low-field MR image data is provided to a second trained neural network (or additional hidden layers of the first neural network) to generate an attenuation (mu) map. The mu-map is applied to the PET image data to perform attenuation correction. The attenuation-corrected PET image data can be output for storage and/or used to generate one or more clinical PET images.

FIG. 1 illustrates one embodiment of a nuclear imaging system 2. The nuclear imaging system 2 includes a scanner for at least a first modality 12 provided in a first gantry 16a. The first modality 12 can include any suitable modality, such as, for example, a computed-tomography (CT) modality, a positron-emission tomography (PET) modality, a single-photon emission computerized tomography (SPECT) modality, etc. The first modality 12 can include a long axial field-of-view (FOV) scanner or a short axial FOV scanner. A patient 17 can lie on a movable patient bed 18 that can be movable with respect to the first gantry 16a and/or can lie on a stationary bed that maintains a fixed position while the gantry 16a is moved with respect to the patient bed 18. In some embodiments, the nuclear imaging system 2 includes a scanner for a second modality 14 provided in a second gantry 16b. The second modality 14 can be any suitable imaging modality, such as, for example, an MR modality, a CT modality, a PET modality, a SPECT modality and/or any other suitable imaging modality. The second modality 14 can include a long axial FOV scanner or a short axial FOV scanner. Each of the first modality 12 and/or the second modality 14 can include one or more detectors 50 configured to detect an annihilation photon, gamma ray, magnetic resonance, and/or other nuclear imaging event.

Scan data from the first modality 12 and/or the second modality 14 is stored at one or more computer databases 40 and processed by one or more computer processors 60 of a computer system 30. The graphical depiction of computer system 30 in FIG. 1 is provided by way of illustration only, and computer system 30 can include one or more separate computing devices, for example, as described with respect to FIG. 2. The scan data can be provided by the first modality 12, the second modality 14, and/or provided as a separate data set, such as, for example, from a memory coupled to the computer system 30. The computer system 30 can include one or more processing electronics for processing a signal received from one of the plurality of detectors 50.

Figure 2:
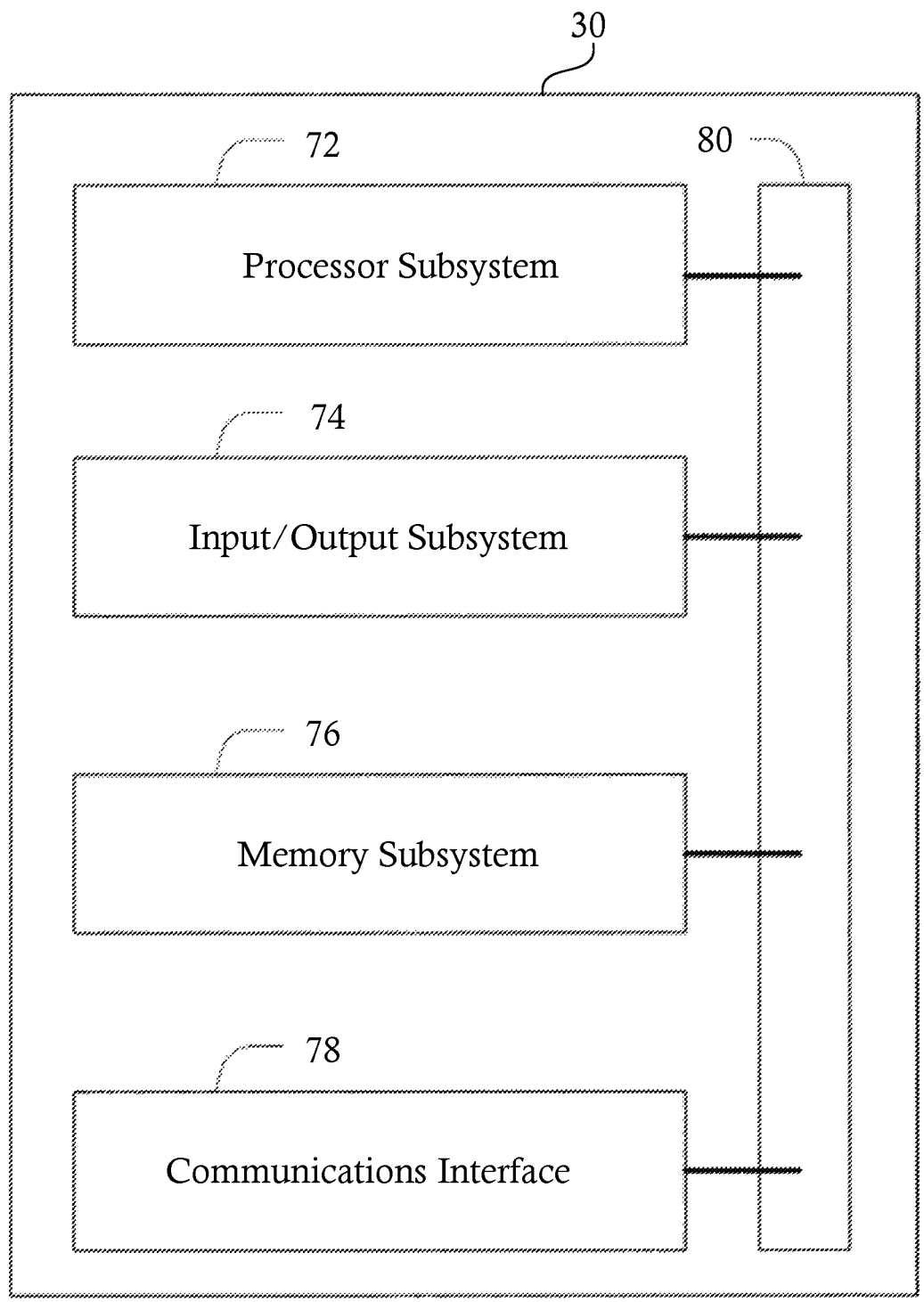
FIG. 2 illustrates a block diagram of a computer system, in accordance with some embodiments.

FIG. 2 illustrates a computer system 30 configured to implement one or more processes, in accordance with some embodiments. The system 30 is a representative device and can include a processor subsystem 72, an input/output subsystem 74, a memory subsystem 76, a communications interface 78, and a system bus 80. In some embodiments, one or more than one of the system 30 components can be combined or omitted such as, for example, not including an input/output subsystem 74. In some embodiments, the system 30 can comprise other components not shown in FIG. 2. For example, the system 30 can also include, for example, a power subsystem. In other embodiments, the system 30 can include several instances of a component shown in FIG. 2. For example, the system 30 can include multiple memory subsystems 76. For the sake of conciseness and clarity, and not limitation, one of each component is shown in FIG. 2.

The processor subsystem 72 can include any processing circuitry operative to control the operations and performance of the system 30. In various aspects, the processor subsystem 72 can be implemented as a general purpose processor, a chip multiprocessor (CMP), a dedicated processor, an embedded processor, a digital signal processor (DSP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor subsystem 72 also can be implemented by a controller, a microcontroller, an application specific integrated circuit (ASIC), a field programmable gate array (FPGA), a programmable logic device (PLD), and so forth.

In various aspects, the processor subsystem 72 can be arranged to run an operating system (OS) and various applications. Examples of an OS comprise, for example, operating systems generally known under the trade name of Apple OS, Microsoft Windows OS, Android OS, Linux OS, and any other proprietary or open source OS. Examples of applications comprise, for example, network applications, local applications, data input/output applications, user interaction applications, etc.

In some embodiments, the system 30 can include a system bus 80 that couples various system components including the processing subsystem 72, the input/output subsystem 74, and the memory subsystem 76. The system bus 80 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCM-CIA), Small Computers Interface (SCSI) or other proprietary bus, or any custom bus suitable for computing device applications.

In some embodiments, the input/output subsystem 74 can include any suitable mechanism or component to enable a user to provide input to system 30 and the system 30 to provide output to the user. For example, the input/output subsystem 74 can include any suitable input mechanism, including but not limited to, a button, keypad, keyboard, click wheel, touch screen, motion sensor, microphone, camera, etc.

In some embodiments, the input/output subsystem 74 can include a visual peripheral output device for providing a display visible to the user. For example, the visual peripheral output device can include a screen such as, for example, a Liquid Crystal Display (LCD) screen. As another example, the visual peripheral output device can include a movable display or projecting system for providing a display of content on a surface remote from the system 30. In some embodiments, the visual peripheral output device can include a coder/decoder, also known as Codecs, to convert digital media data into analog signals. For example, the visual peripheral output device can include video Codecs, audio Codecs, or any other suitable type of Codec.

The visual peripheral output device can include display drivers, circuitry for driving display drivers, or both. The visual peripheral output device can be operative to display content under the direction of the processor subsystem 72. For example, the visual peripheral output device can be able to play media playback information, application screens for application implemented on the system 30, information regarding ongoing communications operations, information regarding incoming communications requests, or device operation screens, to name only a few.

In some embodiments, the communications interface 78 can include any suitable hardware, software, or combination of hardware and software that is capable of coupling the system 30 to one or more networks and/or additional devices. The communications interface 78 can be arranged to operate with any suitable technique for controlling information signals using a desired set of communications protocols, services or operating procedures. The communications interface 78 can include the appropriate physical connectors to connect with a corresponding communications medium, whether wired or wireless.

Vehicles of communication comprise a network. In various aspects, the network can include local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules can communicate in accordance with a number of wired protocols. Examples of wired protocols can include Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 78 can include one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 78 can include a wireless interface comprising one or more antennas, transmitters, receivers, transceivers, amplifiers, filters, control logic, and so forth.

In various aspects, the communications interface 78 can provide data communications functionality in accordance with a number of protocols. Examples of protocols can include various wireless local area network (WLAN) protocols, including the Institute of Electrical and Electronics Engineers (IEEE) 802.xx series of protocols, such as IEEE 802.11a/b/g/n/ac, IEEE 802.16, IEEE 802.20, and so forth. Other examples of wireless protocols can include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols can include wireless personal area network (PAN) protocols, such as an Infrared protocol, a protocol from the Bluetooth Special Interest Group (SIG) series of protocols (e.g., Bluetooth Specification versions 5.0, 6, 7, legacy Bluetooth protocols, etc.) as well as one or more Bluetooth Profiles, and so forth. Yet another example of wireless protocols can include near-field communication techniques and protocols, such as electro-magnetic induction (EMI) techniques. An example of EMI techniques can include passive or active radio-frequency identification (RFID) protocols and devices. Other suitable protocols can include Ultra Wide Band (UWB), Digital Office (DO), Digital Home, Trusted Platform Module (TPM), ZigBee, and so forth.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein. This computer-readable storage medium can be embodied in memory subsystem 76.

In some embodiments, the memory subsystem 76 can include any machine-readable or computer-readable media capable of storing data, including both volatile/non-volatile memory and removable/non-removable memory. The memory subsystem 76 can include at least one non-volatile memory unit. The non-volatile memory unit is capable of storing one or more software programs. The software programs can contain, for example, applications, user data, device data, and/or configuration data, or combinations therefore, to name only a few. The software programs can contain instructions executable by the various components of the system 30.

In various aspects, the memory subsystem 76 can include any machine-readable or computer-readable media capable of storing data, including both volatile/non-volatile memory and removable/non-removable memory. For example, memory can include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In one embodiment, the memory subsystem 76 can contain an instruction set, in the form of a file for executing various methods, such as methods including A/B testing and cache optimization, as described herein. The instruction set can be stored in any acceptable form of machine readable instructions, including source code or various appropriate programming languages. Some examples of programming languages that can be used to store the instruction set comprise, but are not limited to: Java, C, C++, C#, Python, Objective-C, Visual Basic, or .NET programming. In some embodiments a compiler or interpreter is comprised to convert the instruction set into machine executable code for execution by the processing subsystem 72.

FIGS. 3-6 illustrate various embodiments of modality arrangements 90a-90d for multi-modality imaging systems, such as the imaging system described above with respect to FIG. 1. The modality arrangements each including a first imaging modality 12, such as a PET imaging modality, and a second imaging modality 14a-14d, such as a low-field MR imaging modality. Although embodiments are discussed herein including a PET imaging modality, it will be appreciated that the first imaging modality may be any suitable single imaging modality, such as PET, SPECT, CT, etc., and/or any suitable hybrid imaging modality, such as PET/CT scanner, SPECT/PET scanner, etc.

Low-field MR imaging systems include magnetic resonance imaging systems that have lower field strengths than currently used in clinical settings. For example, in various embodiments, a low-field MR modality may have a field strength less than about 0.2 T up to about 1 T, although it will be appreciated that any suitable field strength may be applied that is less than typical clinical field strengths, such as, for example, any field strength less than about 1.5 T, less than about 3 T, etc.

The use of a low-field MR imaging modality 14a-14d allows for lower initial costs for multi-modality imaging systems. For example, low-field MR imaging modalities 14a-14d have a lower cost of equipment (e.g., due to lower field strengths, lack of dedicated cooling mechanisms) and a lower cost of facility/installation requirements (e.g., low-field MR imaging modalities 14a-14d do not require the in-room shielding necessary with conventional MR imaging modalities, lower space requirements due to smaller footprint compared to conventional MR imaging systems, etc.). Further, low-field MR imaging modalities 14a-14d have lower operational costs. For example, conventional MR imaging modalities require the use of a chiller or cryogenic cooling device whereas low-field MR imaging modalities 14a-14d can forego such cooling mechanisms.

The use of low-field MR allows the use of an open design low-field MR imaging modality 14b, 14d (e.g., as used in modality arrangements 90b, 90d and as discussed below with respect to FIGS. 4 and 6). An open-bore MR imaging modality 14b, 14d allows access to a patient for interventional and/or radiotherapy procedures during MR imaging, increasing patient comfort, clinical access, and patient outcomes. The lower field strength of low-field MR imaging modalities 14a-14d provides a lower energy deposition (e.g., specific absorption rate (SAR)) in patient tissue. Low-field MR imaging modalities 14a-14d provide a reduction in chemical shift, susceptibility, and flow/motion artifacts and further provide improved imaging when used in conjunction with metal implants.

As discussed below, the use of a low-field MR imaging modalities 14a-14d may eliminate the need to use other imaging modalities for attenuation correction. For example, in some embodiments, a low-field MR imaging modality may be used in place of a CT imaging modality to provide a second set of image data for use in attenuation correction of PET image data captured using a PET imaging modality. The use of an MR imaging modality, as compared to a CT imaging modality, eliminates the need for a patient to receive a CT radiation dose.

In some embodiments, a low-field MR imaging modality may be adapted primarily for generating mu-maps for attenuation correction of PET image data. For example, in some embodiments, magnetic field strength, gradient strength, parameters of receiver coils (e.g., materials, number, locations, etc.), and/or parameters of the low-field MR imaging modality may be reduced to levels insufficient for generating images for clinical use but sufficient for generating a mu-map. Each of the reduced parameters may be further optimized, independently or collectively, for mu-map generation. In some embodiments, sampling efficiency of the low-field MR imaging modality may be increased by performing longer scans (at lower field strengths) as compared to convention MR imaging modalities.

In some embodiments, the receive elements in a low-field MR imaging modality (e.g., RF coil architecture, magnetic field gradient design, etc.), in conjunction with the processes disclosed herein using improved image reconstruction algorithms, allow the use of low-field MR imaging modalities (and the related low-field strengths) to achieve acceptable image quality for attenuation correction of PET image data. Using multiple receive elements in a low-field MR imaging modality provides for more efficient sampling through parallel imaging and simultaneous multi-slice (SMS) acquisitions, as compared to conventional MR imaging modalities. Sampling in a low-field MR imaging modality may be further improved using compressed sensing techniques and higher bandwidth-time product RF pulses (as RF power deposition scales with the square of the magnetic field of the MR imaging modality).

Figure 3:
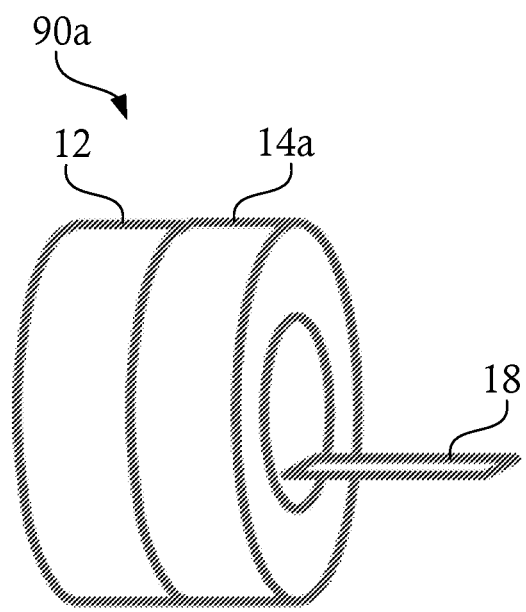
FIG. 3 illustrates a multi-modality imaging system having a PET imaging ring and an MR imaging ring concentrically and linearly aligned, in accordance with some embodiments.

FIG. 3 illustrates a modality arrangement 90a including the PET imaging modality 12 and the MR imaging modality 14a arranged in a "washer-dryer" configuration in which the bore of the PET imaging modality 12 and the bore of the MR imaging modality 14a are coaxially aligned and the imaging modalities 12, 14a are positioned spatially adjacent and in-contact such that a patient may traverse through each of the imaging modalities simultaneously (or in series) without moving the patient bed 18 and/or relocating the patient 17.

Figure 4:
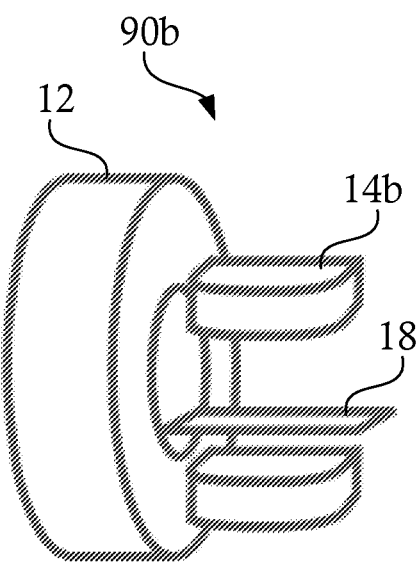
FIG. 4 illustrates a multi-modality imaging system having a PET imaging ring and an open bore MR imaging system concentrically and linearly aligned.

FIG. 4 illustrates a similar modality arrangement 90b as illustrated in FIG. 3, but the low-field MR imaging modality 14b is an open-bore imaging modality. Open-bore imaging modalities provide lower field strength and lower quality images. Although the image quality of the low-field open-bore MR imaging modality 14b may not be sufficient for diagnostic imaging, the low-field MR imaging modality 14b provides sufficient quality for attenuation correction and registration of another imaging modality, such as the PET imaging modality 14a.

Figure 5:
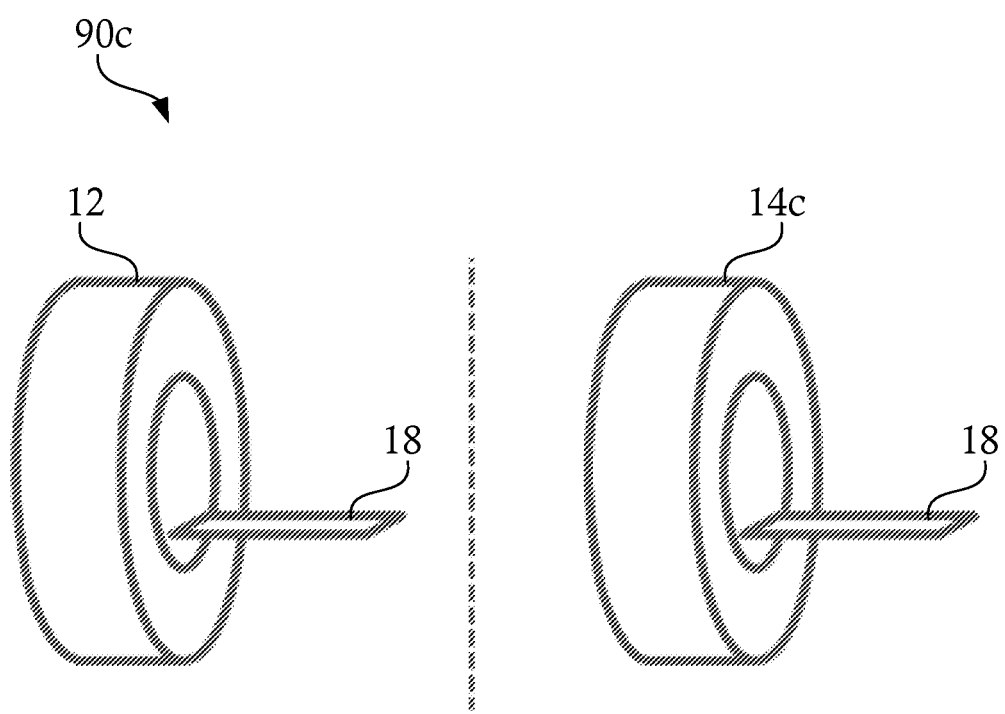
FIG. 5 illustrates a multi-modality imaging system having a PET imaging ring and a spatially separated MR imaging ring, in accordance with some embodiments.
Figure 6:
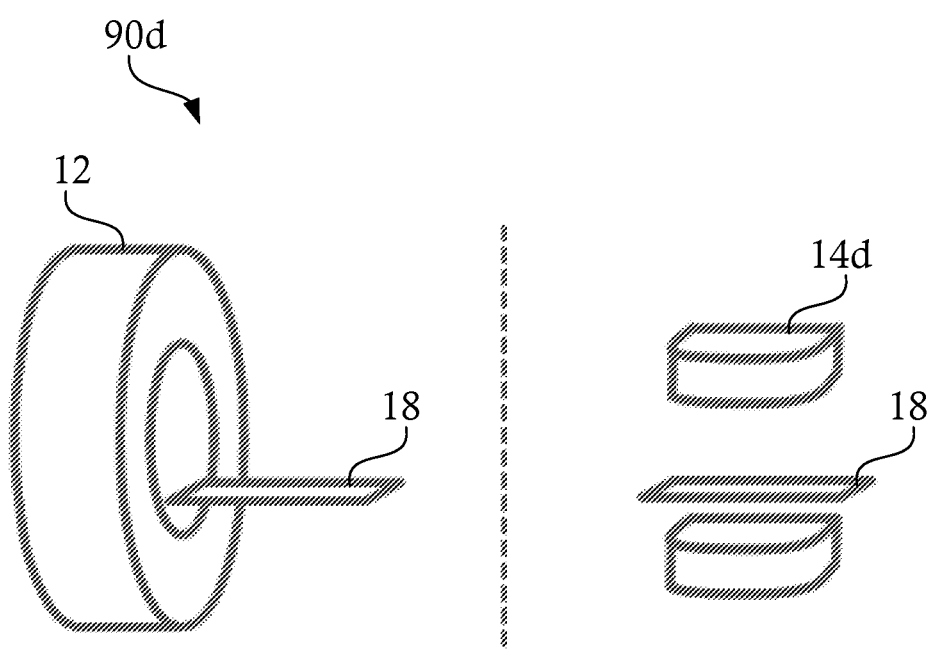
FIG. 6 illustrates a multi-modality imaging system having a PET imaging ring and a spatially separated open bore MR imaging system, in accordance with some embodiments.

FIGS. 5 and 6 illustrate modality arrangements 90c-90d in which the PET imaging modality 12 is spatially separated from the MR imaging modality 14c-14d. Spatially separating the imaging modalities 12, 14c-14d allows a patient to be imaged in a first imaging modality, such as PET imaging modality 12, at a first time and imaged in a second imaging modality, such as MR imaging modality 14c-14d at a second time. In other embodiments, separate imaging modalities may be used in locations in which space is a premium, with the separate imaging modalities being switched for various imaging procedures within the same space.

Figure 7:
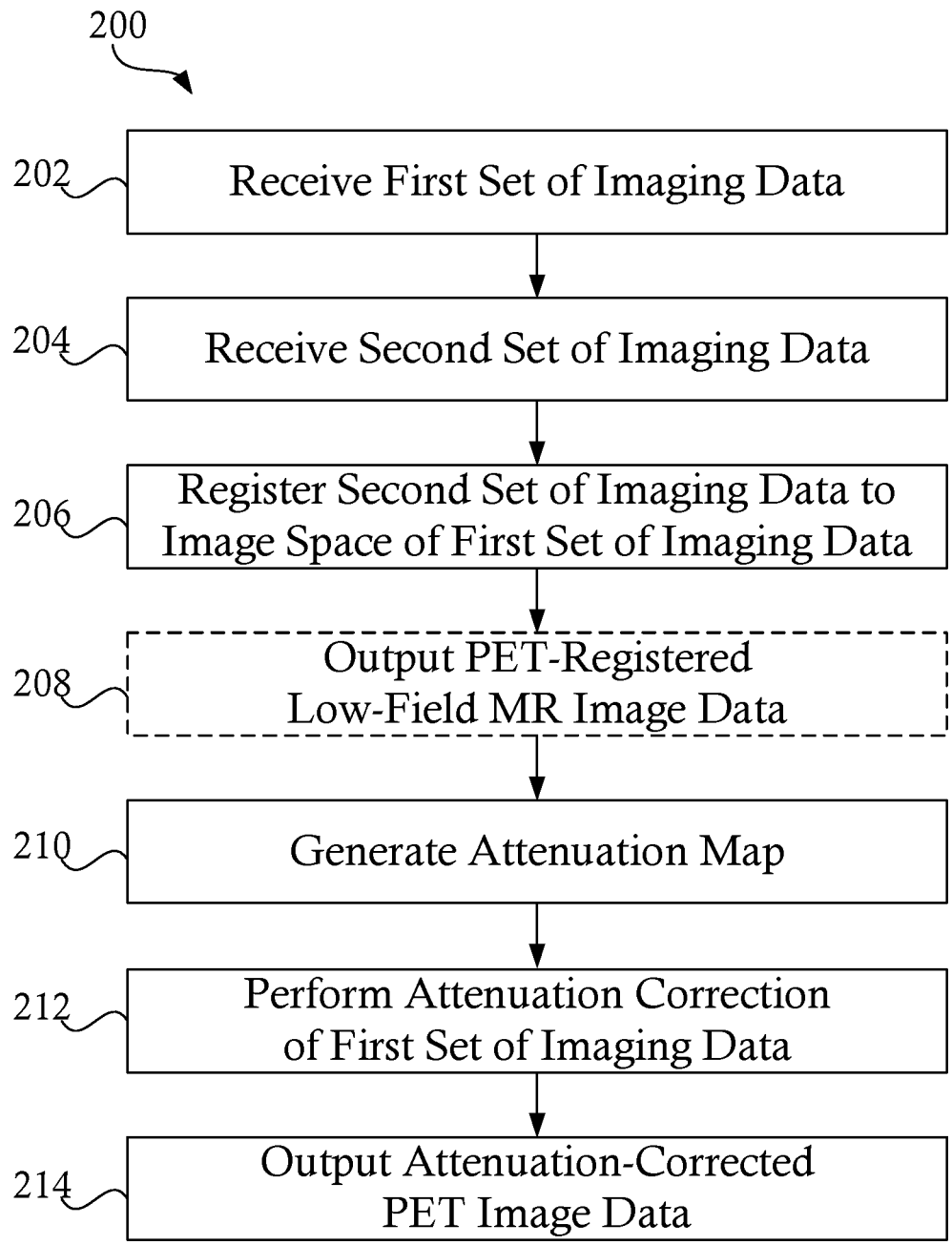
FIG. 7 is a flowchart illustrating a method of attenuation correction of PET image data using low-field MR image data, in accordance with some embodiments.
Figure 8:
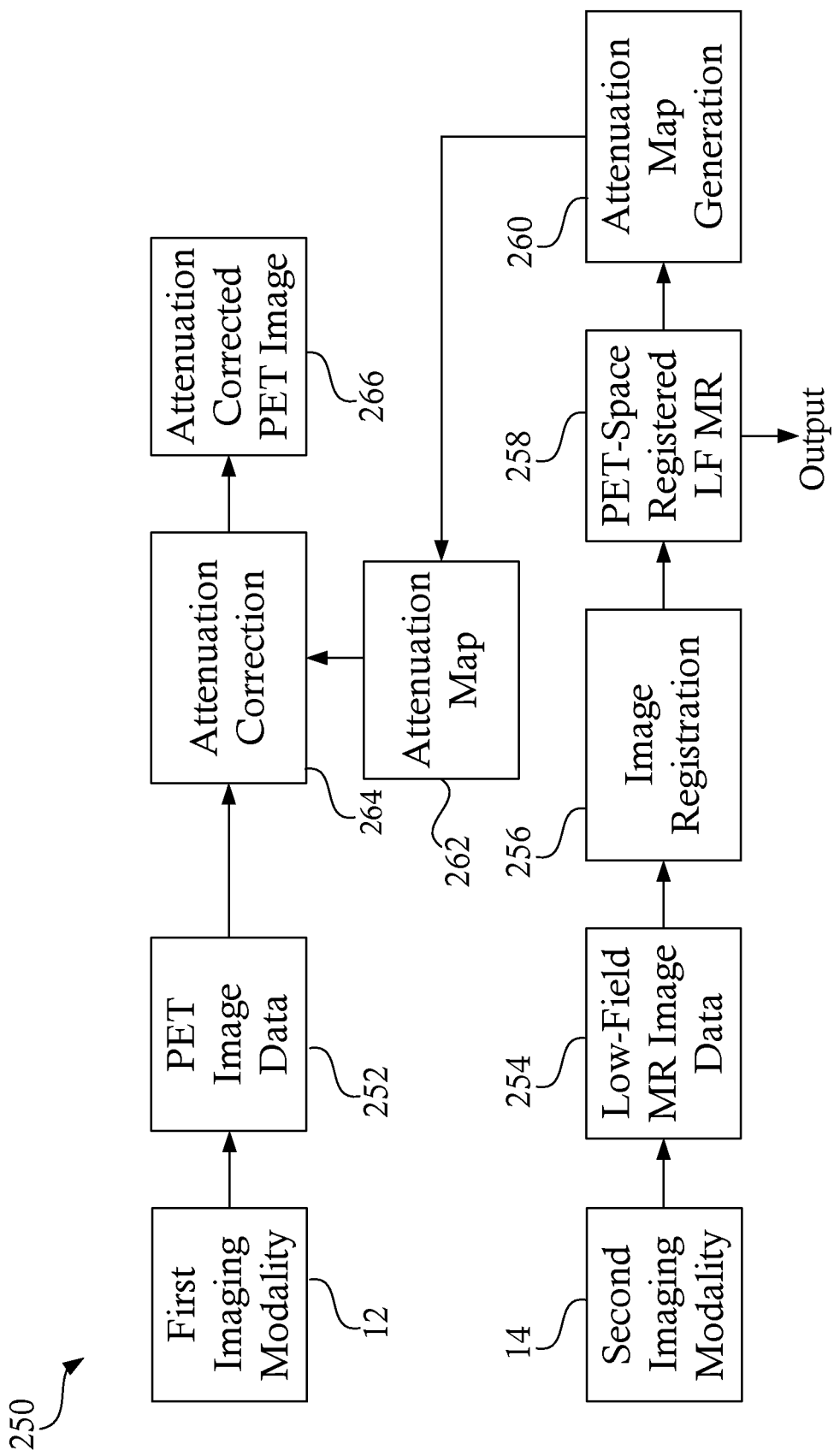
FIG. 8 is a process diagram illustrating various steps of the method of FIG. 7, in accordance with some embodiments.

In some embodiments, a low-field MR imaging modality, such as one of the low-field MR imaging modalities 14a-14d illustrated in FIGS. 3-6, is configured to provide a set of low-field MR image data to be used for attenuation correction of a PET image data obtained by the PET imaging modality 12. FIG. 7 is a flowchart 200 illustrating a method of attenuation correction of PET image data using low-field MR image data, in accordance with some embodiments. FIG. 8 is a process diagram 250 illustrating various steps of the method of FIG. 7, in accordance with some embodiments. Any of the modality arrangements 90a-90d may be used to implement any of the following methods and/or processes.

At step 202, a first set of image data, such as PET image data 252, is obtained using a first imaging modality 12, such as, for example, a PET imaging modality. At step 204, a set of low-field MR image data is obtained using a low-field MR imaging modality 14a-14d. The PET image data 252 and/or the low-field MR image data 254 may be obtained directly from the respective imaging modalities 12, 14a-14d and/or may be stored in and obtained from a non-transient storage, such as, for example, the computer database 40.

At step 206, an image registration module 256 performs image registration to register, e.g., spatially align, the low-field MR image data to the PET image data. The image registration module 256 generates a set of PET-space registered low-field MR image data 258. The image registration module 256 may include a trained neural network and/or a conventional image registration algorithm. For example, in some embodiments, a trained neural network can include a neural network trained using a set of training data including pre-registered and/or aligned data sets. The trained neural network may be configured to apply any suitable image registration process, such as, for example, anatomical landmarking, deep reinforcement learning processes, image synthesis using generative adversarial networks (independently and/or followed by conventional registration), unsupervised learning approaches, and/or any other suitable process.

In some embodiments, the neural network is trained using one or more training methods configured to compensate for gradient nonlinearity and magnet inhomogeneity in the low-field MR imaging modality. For example, in some embodiments, gradient and magnet nonlinearities may be incorporated directly into a reconstruction process (used as part of an image registration process), such as, for example, using MR fingerprinting to model inhomogeneities and alleviate the need for a homogenous gradient, RF, and $B_0$ field. Compensating for gradient and/or magnet nonlinearities provides for the reduction of dictionaries and higher efficiency at lower field strengths. Embodiments including a trained neural network and/or a conventional image registration algorithm may be used with any of the foregoing and/or any of the following embodiments.

Figure 9:
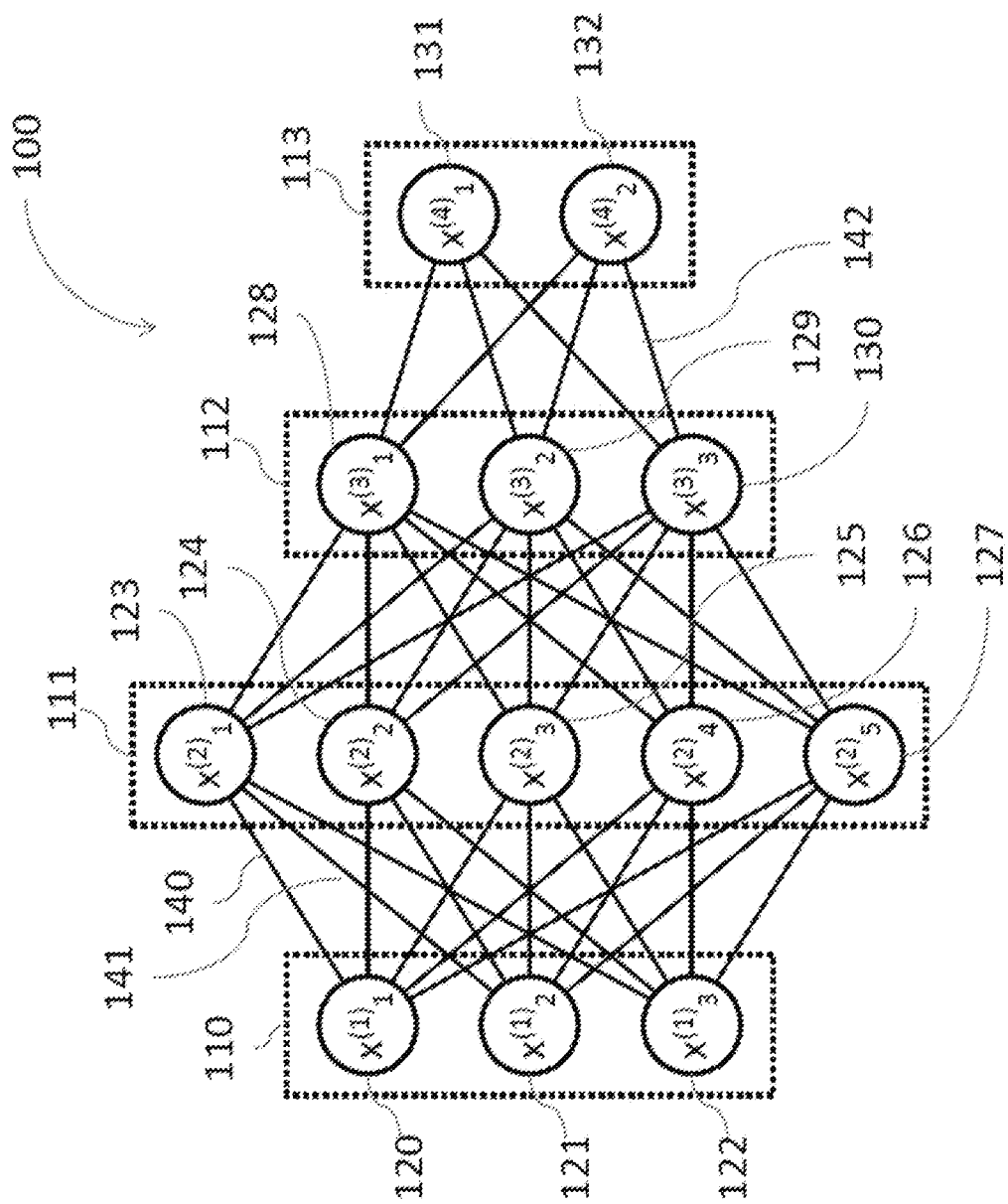
FIG. 9 illustrates an embodiment of an artificial neural network, in accordance with some embodiments.

FIG. 9 displays an embodiment of an artificial neural network 100, in accordance with some embodiments. Alternative terms for "artificial neural network" are "neural network," "artificial neural net," "neural net," or "trained function." The artificial neural network 100 comprises nodes 120-132 and edges 140-142, wherein each edge 140-142 is a directed connection from a first node 120-132 to a second node 120-132. In general, the first node 120-132 and the second node 120-132 are different nodes 120-132, although it is also possible that the first node 120-132 and the second node 120-132 are identical. For example, in FIG. 2 the edge 140 is a directed connection from the node 120 to the node 123, and the edge 142 is a directed connection from the node 130 to the node 132. An edge 140-142 from a first node 120-132 to a second node 120-132 is also denoted as "ingoing edge" for the second node 120-132 and as "outgoing edge" for the first node 120-132.

In this embodiment, the nodes 120-132 of the artificial neural network 100 can be arranged in layers 110-113, wherein the layers can comprise an intrinsic order introduced by the edges 140-142 between the nodes 120-132. In particular, edges 140-142 can exist only between neighboring layers of nodes. In the displayed embodiment, there is an input layer 110 comprising only nodes 120-122 without an incoming edge, an output layer 113 comprising only nodes 131, 132 without outgoing edges, and hidden layers 111, 112 in-between the input layer 110 and the output layer 113. In general, the number of hidden layers 111, 112 can be chosen arbitrarily. The number of nodes 120-122 within the input layer 110 usually relates to the number of input values of the neural network, and the number of nodes 131, 132 within the output layer 113 usually relates to the number of output values of the neural network.

In particular, a (real) number can be assigned as a value to every node 120-132 of the neural network 100. Here, $x^{(n)}_i$ denotes the value of the i-th node 120-132 of the n-th layer 110-113. The values of the nodes 120-122 of the input layer 110 are equivalent to the input values of the neural network 100, the values of the nodes 131, 132 of the output layer 113 are equivalent to the output value of the neural network 100. Furthermore, each edge 140-142 can comprise a weight being a real number, in particular, the weight is a real number within the interval [−1, 1] or within the interval [0, 1]. Here, $w^{(m,n)}_{i,j}$ denotes the weight of the edge between the i-th node 120-132 of the m-th layer 110-113 and the j-th node 120-132 of the n-th layer 110-113. Furthermore, the abbreviation $w^{(n)}_{i,j}$ is defined for the weight $w^{(n,n+1)}_{i,j}$.

In particular, to calculate the output values of the neural network 100, the input values are propagated through the neural network. In particular, the values of the nodes 120-132 of the (n+1)-th layer 110-113 can be calculated based on the values of the nodes 120-132 of the n-th layer 110-113 by $$x_j^{(n+1)} = f(\Sigma_i x_i^{(n)} \cdot w_{i,j}^{(n)})$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 110 are given by the input of the neural network 100, wherein values of the first hidden layer 111 can be calculated based on the values of the input layer 110 of the neural network, wherein values of the second hidden layer 112 can be calculated based in the values of the first hidden layer 111, etc.

In order to set the values $w^{(m,n)}_{i,j}$ for the edges, the neural network 100 has to be trained using training data. In particular, training data comprises training input data and training output data (denoted as $t_i$). For a training step, the neural network 100 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 100 (backpropagation algorithm). In particular, the weights are changed according to $$w'_{i,j}{}^{(n)} = w_{i,j}{}^{(n)} - \gamma \cdot \delta_j^{(n)} \cdot x_i^{(n)}$$

wherein γ is a learning rate, and the numbers $\delta^{(n)}{}_j$ can be recursively calculated as $$\delta_j^{(n)} = (\Sigma_k \delta_k^{(n+1)} \cdot w_{j,k}{}^{(n+1)}) \cdot f'(\Sigma_i x_i^{(n)} \cdot w_{i,j}{}^{(n)})$$

based on $\delta^{(n+1)}{}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}{}^{(n)})$$

if the (n+1)-th layer is the output layer 113, wherein f' is the first derivative of the activation function, and $y^{(n+1)}{}_j$ is the comparison training value for the j-th node of the output layer 113.

In some embodiments, at optional step 208, the set of PET-space registered MR image data is output for use in one or more future reconstructions, for training or re-training of a neural network, and/or for use in any other suitable process. For example, in some embodiments, the low-field MR image data lacks the requisite definition for generation of clinical images, but may be used to assist in generation of other clinical images, such as generation of a mu-map for attenuation correction of PET image data, as discussed below. In other embodiments, the low-field MR image data may be linked to clinician-approved and labeled reconstructed images, such as attenuation-corrected PET reconstructed images having one or more anomalies labeled by a clinician. The labeled low-field MR images may be used to further refine or train the neural network configured to provide image registration using one or more training or reinforcement processes, as discussed above. The optional output of the PET-space registered MR image data may be integrated into any of the foregoing or any of the following embodiments.

At step 210, a mu-map 262 is generated by a mu-map generation process 260 from the set of PET-space registered low-field MR image data 258. The mu-map 262 may be generated using a second trained neural network. In some embodiments, the mu-map generation process 260 is configured to apply a maximum-likelihood reconstruction of activity and attenuation (MLAA) algorithm, although it will be appreciated that mu-map 262 may be generated according to any one or more suitable attenuation-map generation processes. In some embodiments, a trained neural network may utilize templates, atlas information, direct segmentation of MR data, and/or segmentation of images to generate a mu-map. A trained neural network and/or a conventional mu-map generation process may be used with any of the foregoing and/or following embodiments.

In some embodiments, a single trained network may be configured to perform image registration and mu-map generation, either simultaneously and/or sequentially. For example, in some embodiments, a first set of hidden layers may be configured to perform registration of the low-field MR image data to the PET image data and a second set of hidden layers may be configured to generate a mu-map from the PET-space registered low-field MR image data. In some embodiments, a single set of hidden layers performs image registration and mu-map generation simultaneously. A single trained neural network may be used with any of the foregoing and/or following embodiments.

At step 212, the generated mu-map 262 is used for attenuation correction 264 of the PET image data 252 to generate at least one attenuation-corrected PET image 266.

Attenuation correction may be performed using any suitable process, such as, for example, using one or more known attenuation correction processes. In some embodiments, a neural network may be trained to perform attenuation correction based on the generated mu-map 262. It will be appreciated that any suitable attenuation correction process 264 may be applied to correct the PET image data 252. The attenuation correction process 264 generates at least one attenuation corrected PET image 266 and/or a set of attenuation corrected PET image data. The at least one attenuation corrected PET image 266 and/or the set of attenuation corrected PET image data can be output, at step 214, for storage on a storage device (such as computer database 40), for later retrieval and use, and/or may be provided for use in clinical and/or diagnostic procedures.

Figure 10:
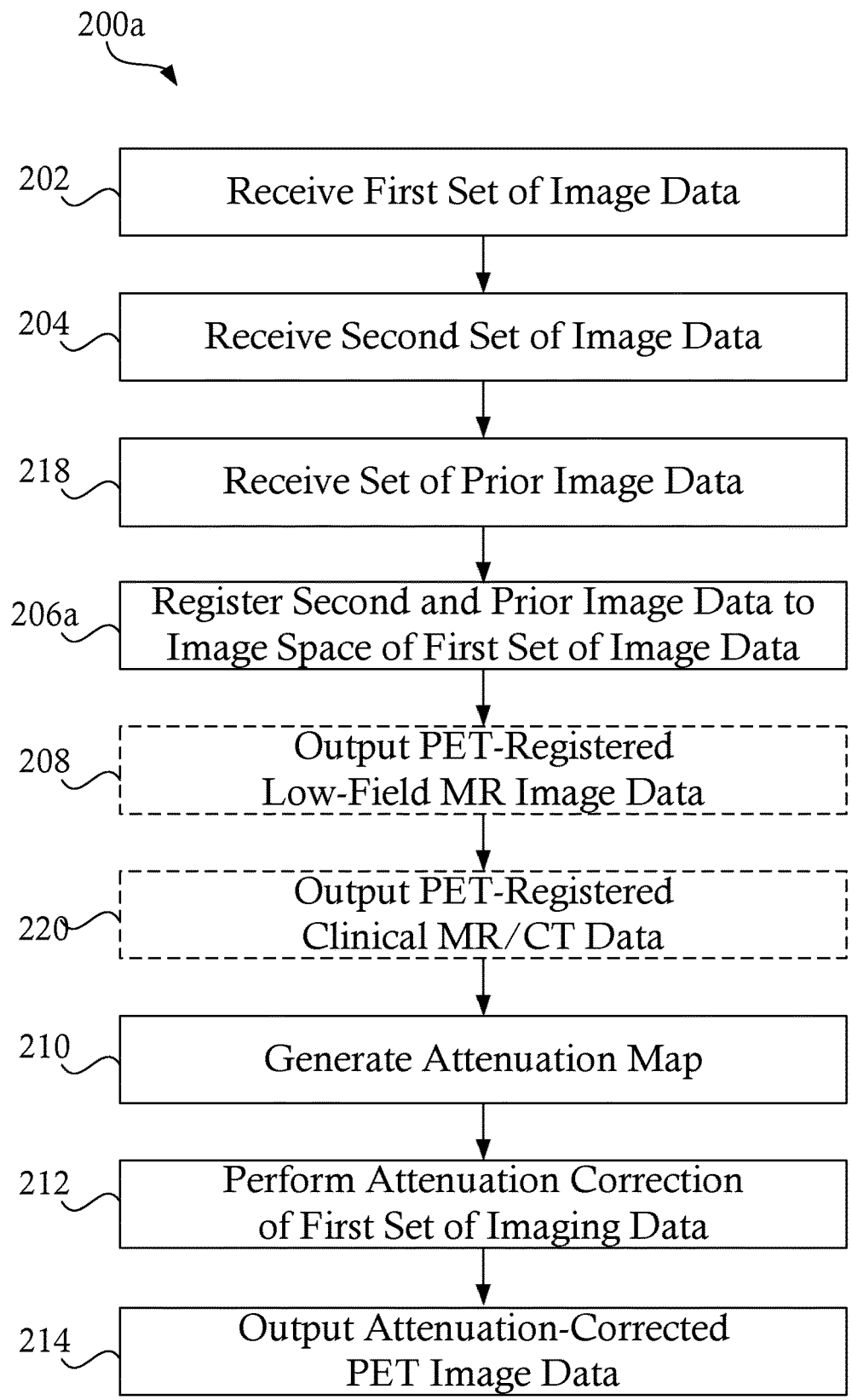
FIG. 10 is a flowchart illustrating a method of attenuation correction of PET image data using low-field MR image data and a prior set of image data, in accordance with some embodiments.
Figure 11:
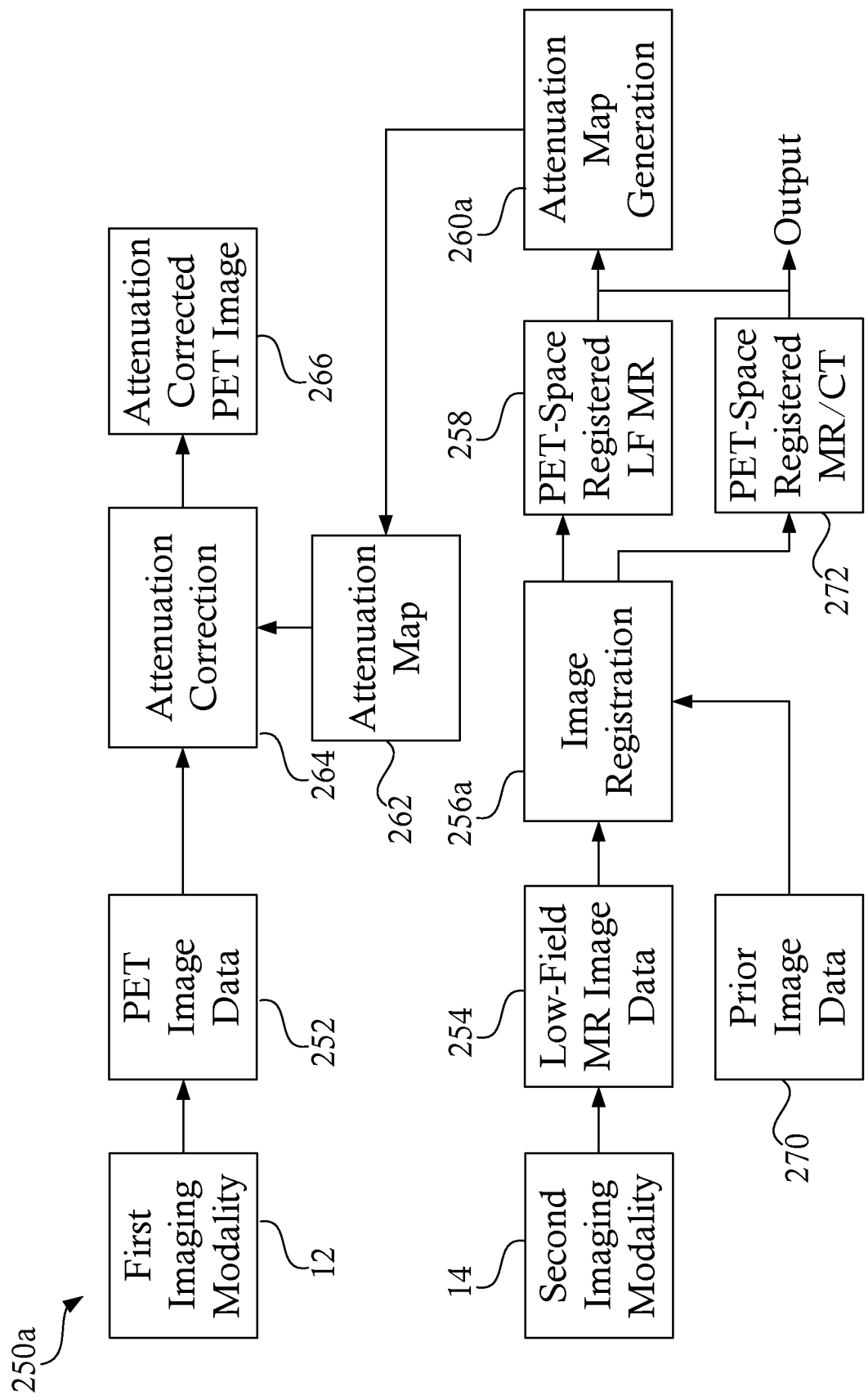
FIG. 11 is a process diagram illustrating various steps of the method of FIG. 10, in accordance with some embodiments.

FIG. 10 is a flowchart 200a illustrating a method of attenuation correction of PET image data using low-field MR image data and prior image data, in accordance with some embodiments. FIG. 11 is a process flow 250a illustrating various steps of the method of FIG. 10, in accordance with some embodiments, flowchart 200a and process flow 250a are similar to flowchart 200 and process flow 250, respectively, discussed above in conjunction with FIGS. 7-8, and similar description is not repeated herein. At step 218, a set of prior image data 270 is received. The set of prior (e.g., existing) image data 270 may include, for example, conventional MR image data and/or CT image data of a patient generated during one or more prior imaging studies. The set of prior image data may be received from a storage device, such as, for example, the computer database 40.

At step 206a, the low-field MR image data 254 and the set of prior image data 270 are registered to the image space of the PET image data 252 by a first trained neural network 256a. The first neural network 256a may be configured to perform registration of the low-field MR image data 254 and the set of prior image data in any suitable order. For example, in some embodiments, the set of low-field MR image data 254 may be registered to the image space of the set of prior image data 270 in a first step and the image space of the set of prior image data is registered to the image space of the set of PET image data 252 in a second step. As another example, in some embodiments, the set of prior image data 270 may be registered to the image space of the set of low-field MR image data 254 in a first step and the image space of the set of low-field MR image data 254 is registered to the image space of the set of PET image data 252 in a second step. After registering the low-field MR image data 254 and the set of prior image data 270, the process 200a proceeds similar to the process 200 discussed above. The second trained neural network 260a is configured to use each of the PET-space registered low-field MR data 258 and the set of PET-space registered MR/CT (e.g., prior) data 272. It will be appreciated that the use of prior image data for registration may be included in any of the foregoing and/or following embodiments.

At optional step 220, the set of PET-space registered prior image data 272 is output. The set of PET-space registered prior image data 272 may include conventional MR image data and/or CT image data registered to the image space of the set of PET image data 252. In some embodiments, the set of PET-space registered prior image data 272 is used to generate one or more clinical images in the image space of the PET image data 252 for comparison to and/or use in conjunction with reconstructed PET images generated at step 214.

In a first embodiment, a computer-implemented method is disclosed. The computer-implemented method includes the steps of receiving a first set of image data and a set of low-field magnetic resonance (MR) image data; generating an attenuation correction map from the low-field MR image data using a first trained neural network; applying at least one attenuation correction process to the first set of image data based on the attenuation correction map to generate a set of attenuation-corrected image data; and generating at least one clinical image from the set of attenuation-corrected image data.

In any of the subsequent embodiments, the computer-implemented method of the first embodiment may further include a step of registering the set of low-field MR image data to an image space of the first set of image data prior to generating the attenuation correction map. The second trained neural network is configured to register the set of low-field MR image data to the image space of the set of first image data.

In any of the subsequent embodiments, the computer-implemented method of the first embodiment may further include the steps of receiving a set of prior image data obtained non-contemporaneously with the first set of image data and the set of low-field MR image data and registering an image space of a first one of the set of prior image data or the set of low-field MR image data to an image space of a second of the prior image data or the set of low-field MR image data prior to registering the set of low-field MR image data to the image space of the first set of image data. The attenuation correction map is generated from each of the low-field MR image data and the set of prior image data. The set of prior image data comprises one of conventional MR image data or computed-tomography (CT) image data.

In any of the subsequent embodiments, the first set of image data includes a set of positron emission tomography (PET) image data and/or a set of single-photon emission computerized tomography (SPECT) image data. The set of low-field MR image data is generated by a low-field MR imaging modality having a field strength of less than 1 Tesla. The set of low-field MR image data is generated by one of an open-bore low-field MR imaging modality or a closed-bored low-field MR imaging modality. The set of low-field MR image data is generated by one of a low-field MR imaging modality coaxially aligned and spatially adjacent to a first imaging modality configured to generate the first set of image data or a low-field MR imaging modality spatially separated from the first imaging modality.

In any of the subsequent embodiments, the first trained neural network is trained using a set of training data comprising MR image data pre-registered to respective PET image space and is trained using at least one of anatomical landmarking, deep reinforcement learning, image synthesis using generative adversarial networks, unsupervised learning, a combination thereof, or any other neural network architecture.

In a second embodiment, a system is disclosed. The system includes a first imaging modality, a low-field MR imaging modality, and a computer. The computer is configured to implement the computer-implemented method of the first embodiment.

In a third embodiment, a non-transitory computer readable medium storing instructions configured to cause a computer system to execute the steps of the first embodiment of the computer-implemented method is disclosed.

In a fourth embodiment, a computer-implemented method is disclosed. The computer-implemented method includes the steps of receiving a first set of image data, a set of low-field magnetic resonance (MR) image data, and a set of prior imaging data. The set of prior imaging data includes image data obtained non-contemporaneously with the first set of image data and the set of low-field MR image data; generating an attenuation correction map from the set of low-field MR image data and the set of prior image data using a first trained neural network; applying at least one attenuation correction process to the first set of image data based on the attenuation correction map to generate a set of attenuation-corrected image data; and generating at least one clinical image from the set of attenuation-corrected image data.

In any of the subsequent embodiments, the computer-implemented method of the fourth embodiment may further include a step of registering an image space of a first one of the set of prior image data or the set of low-field MR image data to an image space of a second of the prior image data or the set of low-field MR image data. Subsequently, the image space of the set of low-field MR image data and the image space of the prior image data are registered to an image space of the first set of image data. Registration is performed prior to generating the attenuation correction map by the second neural network.

In any of the subsequent embodiments, the first set of image data includes a set of positron emission tomography (PET) image data and/or a set of single-photon emission computerized tomography (SPECT) image data. The set of low-field MR image data is generated by a low-field MR imaging modality having a field strength of less than 1 Tesla. The set of low-field MR image data is generated by one of an open-bore low-field MR imaging modality or a closed-bored low-field MR imaging modality. The set of low-field MR image data is generated by one of a low-field MR imaging modality coaxially aligned and spatially adjacent to a first imaging modality configured to generate the first set of image data or a low-field MR imaging modality spatially separated from the first imaging modality. The set of prior image data comprises one of conventional MR image data or computed-tomography (CT) image data.

In any of the subsequent embodiments, the first trained neural network is trained using a set of training data comprising MR image data pre-registered to respective PET image space and is trained using at least one of anatomical landmarking, deep reinforcement learning, image synthesis using generative adversarial networks, unsupervised learning, a combination thereof, or any other neural network architecture.

In a fifth embodiment, a system is disclosed. The system includes a first imaging modality, a low-field MR imaging modality, and a computer. The computer is configured to implement the computer-implemented method of the fourth embodiment.

In a sixth embodiment, a non-transitory computer readable medium storing instructions configured to cause a computer system to execute the steps of the fourth embodiment of the computer-implemented method is disclosed.

Although the subject matter has been described in terms of exemplary embodiments, it is not limited thereto. Rather, the appended claims should be construed broadly, to include other variants and embodiments, which may be made by those skilled in the art.

What is claimed is:
1. A computer-implemented method, comprising:
receiving a first set of image data and a set of low-field magnetic resonance (MR) image data;
generating an attenuation correction map from the set of low-field MR image data using a first trained neural network, wherein the first trained neural network is trained to compensate for gradient nonlinearity and magnet inhomogeneity in the low-field MR imaging modality; and applying at least one attenuation correction process to the first set of image data based on the attenuation correction map to generate at least one clinical attenuation-corrected image.

2. The computer-implemented method of claim 1, comprising registering the set of low-field MR image data to an image space of the first set of image data prior to generating the attenuation correction map.

3. The computer-implemented method of claim 2, wherein a second trained neural network is configured to register the set of low-field MR image data to the image space of the set of first image data.

4. The computer-implemented method of claim 2, further comprising:

receiving a set of prior image data obtained non-contemporaneously with the first set of image data and the set of low-field MR image data; and registering an image space of a first one of the set of prior image data or the set of low-field MR image data to an image space of a second of the prior image data or the set of low-field MR image data prior to registering the set of low-field MR image data to the image space of the first set of image data, and wherein the attenuation correction map is generated from each of the low-field MR image data and the set of prior image data.

5. The computer-implemented method of claim 4, wherein the set of prior image data comprises one conventional MR image data or computed-tomography (CT) image data.

6. The computer-implemented method of claim 1, wherein the first set of image data comprises a set of positron emission tomography (PET) image data.

7. The computer-implemented method of claim 1, wherein the first set of image data comprises a set of single-photon emission computerized tomography (SPECT) image data.

8. The computer-implemented method of claim 1, wherein the set of low-field MR image data is generated by a low-field MR imaging modality having at least one parameter optimized to obtain image data for mu-map generation.

9. The computer-implemented method of claim 1, wherein the set of low-field MR image data is generated by a low-field MR imaging modality having a field strength of less than 1 Tesla.

10. The computer-implemented method of claim 1, wherein the set of low-field MR image data is generated by an open-bore low-field MR imaging modality.

11. The computer-implemented method of claim 10, wherein the first trained neural network is trained using at least one of anatomical landmarking, deep reinforcement learning, image synthesis using generative adversarial networks, unsupervised learning, or a combination thereof.

12. The computer-implemented method of claim 1, wherein the set of low-field MR image data is generated by a low-field MR imaging modality coaxially aligned and spatially adjacent to a first imaging modality configured to generate the first set of image data.

13. The computer-implemented method of claim 1, wherein the first trained neural network is trained using a set of training data comprising MR image data pre-registered to respective PET image space.

14. A system, comprising:
a first imaging modality;
a low-field magnetic resonance (MR) imaging modality; and
a computer configured to:
receive a first set of image data from the first imaging modality and a set of low-field MR image data from the low-field MR imaging modality;
generate an attenuation correction map from the set of low-field MR image data using a first trained neural network, wherein the first trained neural network is trained to compensate for gradient nonlinearity and magnet inhomogeneity in the low-field MR imaging modality; and
apply at least one attenuation correction process to the first set of image data based on the attenuation correction map to generate at least one clinical attenuation-corrected image.

15. The system of claim 14, wherein the computer is further configured to register the set of low-field MR image data to an image space of the first set of image data prior to generating the attenuation correction map.

16. The system of claim 15, wherein a second trained neural network is configured to register the set of low-field MR image data to the image space of the set of first image data.

17. The system of claim 14, wherein the computer is further configured to:
receive a set of prior image data obtained non-contemporaneously with the first set of image data and the set of low-field MR image data; and
register an image space of a first one of the set of prior image data or the set of low-field MR image data to an image space of a second of the prior image data or the set of low-field MR image data prior to registering the set of low-field MR image data to the image space of the first set of image data, and wherein the attenuation correction map is generated from each of the low-field MR image data and the set of prior image data.

18. The system of claim 14, wherein the first set of image data comprises one of a set of positron emission tomography (PET) image data or a set of single-photon emission computerized tomography (SPECT) image data.

19. The system of claim 14, wherein the set of low-field MR image data is generated by a low-field MR imaging modality having at least one parameter optimized to obtain image data for mu-map generation.

20. A non-transitory computer readable medium storing instructions configured to cause a computer system to execute the steps of:
receiving a first set of image data and a set of low-field magnetic resonance (MR) image data;
generating an attenuation correction map from the set of low-field MR image data using a first trained neural network, wherein the first trained neural network is trained to compensate for gradient nonlinearity and magnet inhomogeneity in the low-field MR imaging modality; and
applying at least one attenuation correction process to the first set of image data based on the attenuation correction map to generate at least one clinical attenuation-corrected image.

* * * * *